(12) United States Patent
Kumano

(10) Patent No.: US 10,143,787 B2
(45) Date of Patent: Dec. 4, 2018

(54) IMPELLER SHAFT TO BEARING INTERFACE FOR CENTRIFUGAL BLOOD PUMP

(71) Applicant: TERUMO KABUSHIKI KAISHA, Toyko (JP)

(72) Inventor: Koko Kumano, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 355 days.

(21) Appl. No.: 15/082,308

(22) Filed: Mar. 28, 2016

(65) Prior Publication Data

US 2016/0206796 A1 Jul. 21, 2016

Related U.S. Application Data

(63) Continuation of application No. PCT/JP2014/083613, filed on Dec. 18, 2014.

(30) Foreign Application Priority Data

Dec. 27, 2013 (JP) .................................. 2013-272888

(51) Int. Cl.
*A61M 1/10* (2006.01)
*A61M 1/16* (2006.01)
(Continued)

(52) U.S. Cl.
CPC ........ *A61M 1/1013* (2014.02); *A61M 1/1036* (2014.02); *A61M 1/1698* (2013.01); *A61M 1/267* (2014.02); *A61M 1/3666* (2013.01); *F04D 1/00* (2013.01); *F04D 13/024* (2013.01); *F04D 29/026* (2013.01); *F04D 29/046* (2013.01); *F04D 29/0465* (2013.01);
(Continued)

(58) Field of Classification Search
CPC ......................... A61M 1/1013; F04D 29/046
See application file for complete search history.

(56) References Cited

U.S. PATENT DOCUMENTS

| 5,399,074 A | * | 3/1995 | Nose ................... F04D 29/0465 |
| | | | 415/900 |
| 5,575,630 A | * | 11/1996 | Nakazawa ............ F04D 13/026 |
| | | | 415/900 |
| 5,683,231 A | * | 11/1997 | Nakazawa ............ F04D 13/026 |
| | | | 415/900 |
| 5,713,730 A | * | 2/1998 | Nose ................... F04D 29/0465 |
| | | | 417/423.12 |

(Continued)

FOREIGN PATENT DOCUMENTS

| JP | 2005058617 A | 3/2005 |
| WO | 2007063843 A1 | 6/2007 |
| WO | 2007063843 A1 | 7/2007 |

OTHER PUBLICATIONS

European Search Report for Application EP14875199.3, dated Jun. 28, 2017.

*Primary Examiner* — Eldon Brockman
(74) *Attorney, Agent, or Firm* — MacMillan, Sobanski & Todd, LLC

(57) ABSTRACT

A centrifugal pump (10) includes a housing (26), an impeller (28) that is rotatably disposed inside the housing (26), a shaft (62) that is provided at a center rotational axis of the impeller (28), and bearings (70) that pivotally support the shaft ends (66). At least one of the shaft ends (66) has surface roughness $R_a$ equal to or less than 0.21 μm and/or surface roughness $R_y$ equal to or less than 1.49 μm.

3 Claims, 3 Drawing Sheets

(51) Int. Cl.
| | |
|---|---|
| *A61M 1/26* | (2006.01) |
| *F04D 13/02* | (2006.01) |
| *F04D 29/02* | (2006.01) |
| *F04D 29/046* | (2006.01) |
| *F04D 29/22* | (2006.01) |
| *A61M 1/36* | (2006.01) |
| *F04D 1/00* | (2006.01) |
| *F04D 29/42* | (2006.01) |

(52) U.S. Cl.
CPC ..... *F04D 29/0467* (2013.01); *F04D 29/2216* (2013.01); *F04D 29/426* (2013.01); *A61M 1/101* (2013.01); *A61M 1/1006* (2014.02); *F05D 2300/2112* (2013.01); *F05D 2300/516* (2013.01)

(56) References Cited

U.S. PATENT DOCUMENTS

| | | | |
|---|---|---|---|
| 5,863,179 A | 1/1999 | Westphal et al. | |
| 5,957,672 A * | 9/1999 | Aber | A61M 1/10 384/907.1 |
| 5,982,064 A * | 11/1999 | Umeda | F16C 21/00 310/61 |
| 6,135,729 A * | 10/2000 | Aber | A61M 1/10 417/356 |
| 6,254,359 B1 * | 7/2001 | Aber | F04D 3/02 417/356 |
| 6,884,210 B2 * | 4/2005 | Nose | A61M 1/1017 600/16 |
| 2003/0233021 A1 * | 12/2003 | Nose | A61M 1/1017 600/16 |

* cited by examiner

IMPELLER SHAFT TO BEARING INTERFACE FOR CENTRIFUGAL BLOOD PUMP

CROSS REFERENCE TO RELATED APPLICATIONS

This application is a continuation of PCT Application No. PCT/JP2014/083613, filed Dec. 18, 2014, based on and claiming priority to Japanese application no. 2013-272888, filed Dec. 27, 2013, both of which are incorporated herein by reference in their entirety.

TECHNICAL FIELD

The present invention relates to a centrifugal pump which delivers liquid such as blood and the like.

BACKGROUND ART

During cardiac surgery, a heart-lung machine is utilized. The heart-lung machine is used by being embedded in an extracorporeal circulation circuit and performs oxygenation of blood drained from a patient, and filtering for elimination of foreign bodies, and the like. There are various types of heart-lung machines (also known as perfusion systems) depending on differences such as the type of gas exchange unit, the type of pump, the position arrangement of pump, and the like. However, a heart-lung machine generally includes a reservoir (for venous blood), an oxygenator, a heat exchanger, a pump, and a plurality of tubes for connecting the components (for example, refer to JP-A-2009-160265).

One type of pump adapted for use in the heart-lung machine is a centrifugal pump which delivers blood by utilizing centrifugal force occurring due to rotations of an impeller. Generally, the centrifugal pump includes a housing, wherein the impeller is rotatably disposed inside the housing by a shaft which is provided at the center rotational axis of the impeller. A bearing on the housing rotatably supports the shaft. In order to reduce the occurrence of a thrombus (blood clot), a centrifugal pump may be used in which the bearing is formed as a pivot bearing.

In a case of the centrifugal pump employing the pivot bearing, however, the occurrence of hemolysis (damage to blood corpuscles) may become more likely due to sliding between the shaft and the pivot bearing. In addition, a thrombus may be formed on a sliding surface between the shaft and the pivot bearing. In a case where a thrombus is formed, there is a possibility of causing resistance against rotations of the impeller.

SUMMARY OF INVENTION

The present invention has been made in consideration of the foregoing problems, and an object thereof is to provide a centrifugal pump which can prevent hemolysis from being formed due to sliding between a shaft and a pivot bearing and can prevent a thrombus from being formed at shaft ends of the shaft.

In order to achieve the object, according to the present invention, there is provided a centrifugal pump including a housing, an impeller that is rotatably disposed inside the housing, a shaft that is provided at a center rotational axis of the impeller, and bearings that respectively and pivotally support shaft ends provided on opposite ends of the shaft in an axial direction. At least one of the shaft ends has a surface roughness $R_a$ (arithmetic average roughness) equal to or less than 0.21 μm or surface roughness $R_y$ (maximum height) equal to or less than 1.49 μm. More specifically, surface roughness $R_a$ is the average value of the absolute value of the difference between the surface height at each point along the surface and a line that defines the ideal surface. Surface roughness $R_y$ is the height difference between the maximum positive deviation (highest peak) and maximum negative deviation (lowest valley) from the ideal surface.

According to the configuration of the present invention, the surface roughness of at least one of the shaft ends of the shaft is properly set. Therefore, it is possible to prevent hemolysis from occurring due to sliding between the shaft and the bearings, and it is possible to prevent a thrombus from being formed at the shaft ends of the shaft.

In the centrifugal pump, each of the shaft ends may have the surface roughness $R_a$ equal to or less than 0.21 μm or the surface roughness $R_y$ equal to or less than 1.49 μm. Accordingly, it is possible to prevent an occurrence of hemolysis and formation of a thrombus at both ends of the shaft. Therefore, it is possible to further enhance a hemolysis prevention effect and a thrombus prevention effect.

In the centrifugal pump of the invention, the desired surface roughness can be obtained in particular by forming the shaft from alumina ceramic, for example. Alternatively, the shaft may be comprised of other biocompatible materials. In some instances, polishing or other known manufacturing processes can be utilized to provide the desired roughness at the ends of the shaft. Together with a hemolysis prevention effect and a thrombus prevention effect obtained by setting the surface roughness $R_a$ or the surface roughness $R_y$ of the shaft ends of the shaft, it is possible to more effectively prevent hemolysis from occurring and to prevent a thrombus from being formed.

According to the centrifugal pump of the present invention, it is possible to prevent hemolysis from being formed due to sliding between the shaft and the bearings, and it is possible to prevent a thrombus from being formed at shaft ends of the shaft.

DESCRIPTION OF EMBODIMENT

Hereinafter, description will be given regarding a preferred embodiment of a centrifugal pump of the present invention, with reference to the accompanying drawings.

Figure 1:
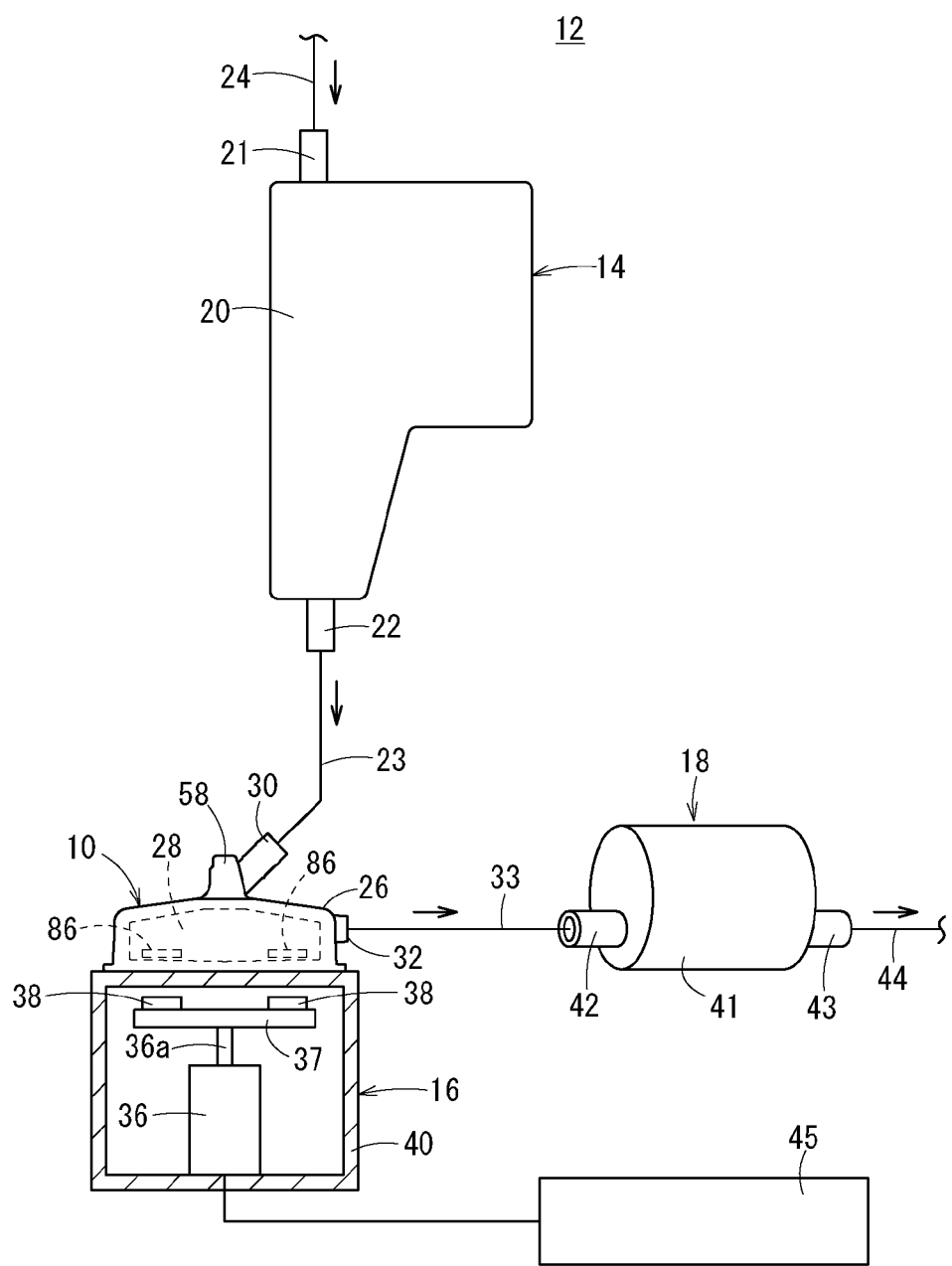
FIG. 1 is a schematic view of a heart-lung machine.

FIG. 1 is a schematic view of a heart-lung machine 12 including a centrifugal pump 10 of the present invention. For example, the heart-lung machine 12 is used for cardiac surgery or the like. The heart-lung machine 12 performs oxygenation of blood drained from a patient, filtering for elimination of foreign bodies, and the like, and then returning the blood to the patient. As illustrated in FIG. 1, the heart-lung machine 12 includes a reservoir 14, a centrifugal pump 10, a pump driving unit 16, and a gas exchange unit 18.

The reservoir 14 temporarily stores blood removed from a patient (venous blood). The reservoir 14 has a reservoir main body 20, a blood inlet port 21 which is provided in an upper portion of the reservoir main body 20 and is connected to a venous line 24 for delivering blood from a blood draining cannula inserted into a patient, and a blood outlet port 22 which is provided in a lower portion of the reservoir main body 20 and is connected to the centrifugal pump 10 via a first connection line 23.

Inside the reservoir main body 20, a blood filter (not illustrated) which filters blood flowing in via the blood inlet port 21 is disposed. Note that, the reservoir main body 20 is also provided with an inlet port (not illustrated) which is connected to a cardiotomy line for delivering blood from the surgical field of a patient.

The centrifugal pump 10 delivers blood from the reservoir 14 to the gas exchange unit 18. The centrifugal pump 10 includes at least a housing 26 and an impeller 28 which is rotatably disposed inside the housing 26. The housing 26 has a blood inlet port 30 which is connected to the blood outlet port 22 of the reservoir 14 via the first connection line 23, and a blood outlet port 32 which is connected to the gas exchange unit 18 via a second connection line 33. For example, the first connection line 23 and the second connection line 33 are flexible and transparent tubes.

Blood flowing into a central portion of the impeller 28 through the blood inlet port 30 flows to an outer circumferential side of the impeller 28 while being accelerated in accordance with rotations of the impeller 28, thereby being discharged through the blood outlet port 32. Note that, the detailed structure of the centrifugal pump 10 will be described later.

The pump driving unit 16 has a motor 36, a rotary member 37 (for example, a rotary plate) which is fixed to a rotary shaft 36a of the motor 36, permanent magnets 38 which are attached to the rotary member 37, and a case 40 which accommodates these components. It is preferable that a plurality of the permanent magnets 38 are provided at substantially equal intervals in the circumferential direction centering around the rotary shaft 36a of the motor 36. For example, the permanent magnets 38 are provided as many as the number of the below-described permanent magnets 86 provided in the centrifugal pump 10.

Due to the above-described configuration of the pump driving unit 16, the permanent magnets 38 provided in the pump driving unit 16 magnetically attract the permanent magnets 86 provided in the centrifugal pump 10. When the motor 36 rotates in such a magnetically attracted state, the permanent magnets 38 rotate together with the motor 36, and the impeller 28 also rotates along with the rotations thereof.

Note that, either an AC motor or a DC motor may be used as the motor 36. However, it is preferable to use a variable speed motor. For example, when a stepping motor is used as the motor 36, it is easy to control the flow rate of blood in the centrifugal pump 10.

The heart-lung machine 12 includes a control unit 45, and the control unit 45 controls driving of the motor 36. In the centrifugal pump 10 which is driven as described above, for example, the impeller 28 can rotate within a range from 0 rpm to 3,000 rpm. When the rotational frequency of the impeller 28 is equal to or lower than 3,000 rpm, it is likely to prevent hemolysis and a thrombus from being formed. Note that, the impeller 28 may be able to rotate equal to or higher than 3,000 rpm.

The gas exchange unit 18 has a main body 41, a blood inlet port 42 which is connected to the blood outlet port 32 of the centrifugal pump 10 via the second connection line 33, and a blood outlet port 43 which is connected to a retransfusion line 44 for returning blood to a patient. The main body 41 adds oxygen to blood flowing in via the blood inlet port 42 and performs gas exchange for eliminating carbon dioxide. Note that, the gas exchange unit 18 may also have a function of heat exchange for changing a blood temperature.

Figure 2:
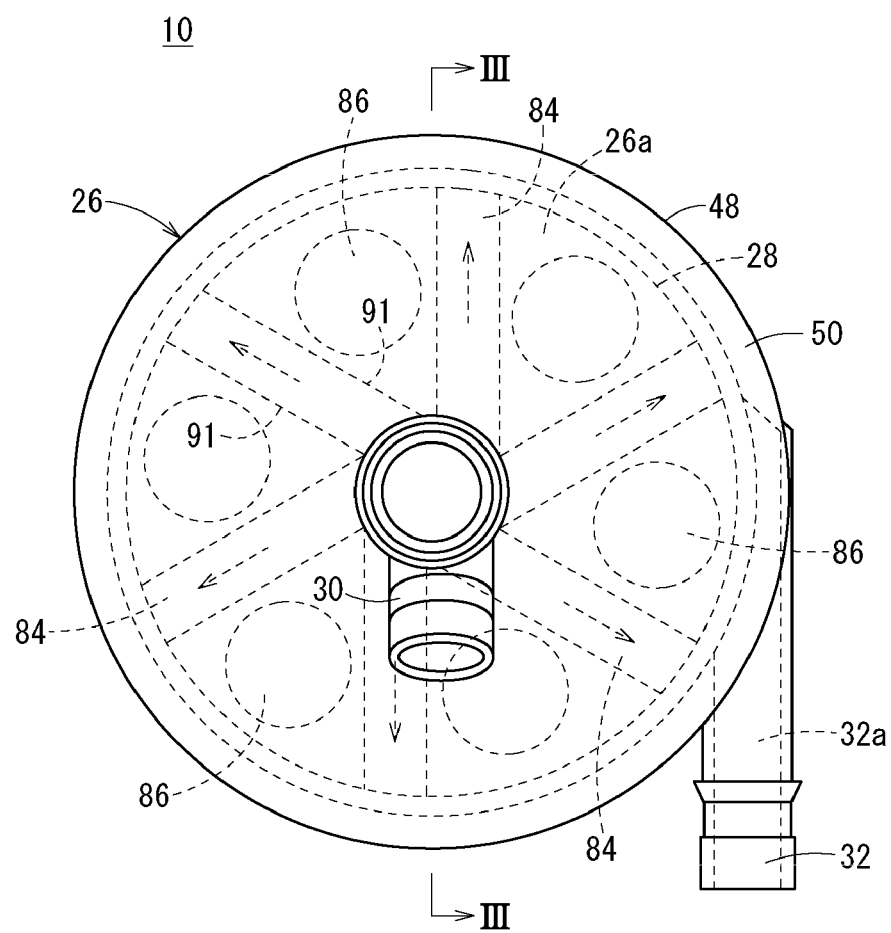
FIG. 2 is a planar view of a centrifugal pump according to an embodiment of the present invention.
Figure 3:
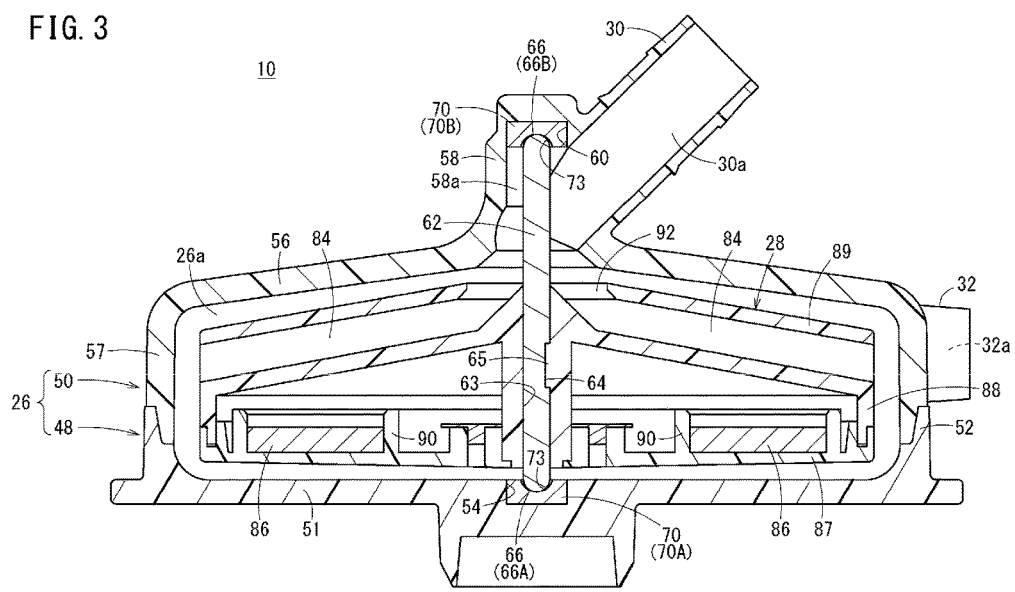
FIG. 3 is a cross-sectional view taken along line III-III in FIG. 2.

FIG. 2 is a planar view of the centrifugal pump 10. FIG. 3 is a cross-sectional view taken along line III-III in FIG. 2.

As illustrated in FIGS. 2 and 3, the housing 26 in the centrifugal pump 10 has a base 48 configuring a lower portion, and a cover 50 configuring an upper portion. The base 48 and the cover 50 form a space 26a (hereinafter, referred to as "the accommodation space 26a") in which the impeller 28 is internally accommodated.

The base 48 has a substantial disk shape in its entirety. As illustrated in FIG. 3, the base 48 has a circular floor 51 and a circumferential wall 52 which protrudes upward from the outer circumferential portion of the floor 51 and continuously encircles the circumference in the circumferential direction. A central portion of the floor 51 is provided with a recessed first disposition portion (i.e., receptacle) 54.

The cover 50 has a disk-shaped ceiling 56 and a circumferential wall 57 which protrudes downward from the outer circumference of the ceiling 56 and continuously encircles the circumference in the circumferential direction. The lower end of the circumferential wall 57 of the cover 50 and the upper end of the circumferential wall 52 of the base 48 are in a state of being fitted with each other and are fixed to each other by appropriate bonding means such as an adhesive and the like. Note that, in FIG. 3, the lower end of the circumferential wall 57 of the cover 50 is fitted with the inner side of the upper end of the circumferential wall 52 of the base 48. However, the upper end of the circumferential wall 52 of the base 48 may be fitted with the inner side of the lower end of the circumferential wall 57 of the cover 50.

The cover 50 is provided with a protruding cylinder portion 58 which protrudes upward from the center of the ceiling 56. The protruding cylinder portion 58 is configured to have a hollow open-bottom structure in which the upper end is closed. Inside an upper portion of the protruding cylinder portion 58, a recessed second disposition portion (i.e., receptacle) 60 is provided.

In addition, the cover 50 is provided with the above-described blood inlet port 30. In the present embodiment, the blood inlet port 30 extends from the protruding cylinder portion 58 in a direction intersecting the protruding cylinder portion 58 (in the illustrated example, in an inclination direction). A lumen 30a of the blood inlet port 30 communicates with the accommodation space 26a via a lumen 58a of the protruding cylinder portion 58.

The cover 50 is also provided with the above-described blood outlet port 32. In the present embodiment, the blood outlet port 32 extends from the outer side surface of the circumferential wall 57 of the cover 50 in a tangential direction. A lumen 32a of the blood outlet port 32 communicates with the accommodation space 26a.

As a configuration material of the housing 26 (the base 48 and the cover 50), for example, it is possible to exemplify various types of resin materials such as various types of glass; polyvinyl chloride; polyethylene; polypropylene; cyclic polyolefin; polystyrene; poly-(4-methylpentene-1); polycarbonate; an acrylic resin; an acrylonitrile-butadiene-styrene copolymer; polyester such as polyethylene terephthalate, polyethylene naphthalate, and the like; a butadiene-styrene copolymer; polyamide (for example, nylon 6, nylon 6,6, nylon 6,10, nylon 12); and the like. It is preferable that the housing 26 is configured to be formed from a transparent material so that blood flowing in the housing 26 can be visually recognized.

In the impeller 28, a plurality of blood induction paths 84 which radially extend from a substantial center of the impeller 28 toward the outer circumferential side are provided. In addition, inside the impeller 28, a plurality of the permanent magnets 86 for transmitting rotating force to the impeller 28 from the outside are provided at substantially equal intervals in the circumferential direction. The blood induction paths 84 are not limited to being straight as illustrated in FIG. 2 and may have curved shapes.

The outer diameter of the impeller 28 is not particularly limited. However, for example, the outer diameter can be set to range approximately from 50 mm to 100 mm. As the outer diameter of the impeller 28 becomes greater, it is more likely to generate high discharge pressure. For example, when the outer diameter of the impeller 28 is equal to or greater than 70 mm, even though the maximum rotational frequency is approximately 3,000 rpm, it is possible to generate comparatively high discharge pressure. As described above, in a case where the rotational frequency is equal to or less than 3,000 rpm, it is likely to prevent hemolysis and a thrombus from being formed. Therefore, when the outer diameter is preferably equal to or greater than 70 mm and the maximum rotational frequency is equal to or less than 3,000 rpm, while preventing hemolysis and a thrombus from being formed, the impeller 28 can generate comparatively high discharge pressure.

In the present embodiment, the impeller 28 has a first rotor 87 which is configured to form the bottom portion, a second rotor 88 which concentrically overlaps the first rotor 87 from above, and a rotor cover 89 which concentrically overlaps the second rotor 88 from above.

The plurality of above-described permanent magnets 86 are respectively held by a plurality of magnet holding portions 90 which are provided on the top surface of the first rotor 87. The plurality of above-described blood induction paths 84 are formed between the second rotor 88 and the rotor cover 89. A plurality of flow channel forming walls 91 which protrude downward from the bottom surface of the rotor cover 89 are configured to form both side walls of the blood induction paths 84. The top surface of the rotor cover 89 has a conical shape, and an opening 92 is formed in a central portion thereof.

A shaft 62 is provided at the central rotational axis of the impeller 28. The shaft 62 is a straight rod-shaped member and has spherically-shaped shaft ends 66 at opposed axial ends. The shaft 62 is fixed to the impeller 28 in a state of being inserted into the insertion hole (i.e., bore) 63 penetrating the central axis of the impeller 28. The shaft 62 and the impeller 28 cannot relatively rotate and are fixed to each other in a state of not being able to be relatively displaced in the axial direction. In the present embodiment, a projection 65 which is provided on the inner circumferential wall forming the insertion hole 63 of the impeller 28 engages with a matching groove 64 which is provided in the shaft 62. Thus, the shaft 62 and the impeller 28 are fixed to each other.

The opposing ends of the shaft 62 respectively protrude downward and upward from the impeller 28. Hereinafter, to discriminate the two shaft ends 66 from each other, the shaft end 66 on the lower side is referred to as "the first shaft end 66A" and the shaft end 66 on the upper side is referred to as "the second shaft end 66B". Each of the shaft ends 66 is set to have a surface roughness $R_a$ (arithmetic average roughness) equal to or less than 0.21 μm and/or a surface roughness $R_y$ (maximum height) equal to or less than 1.49 μm, at least at the surfaces of shaft ends 66 which contact respective pivot bearings. It is preferable that each of the shaft ends 66 is set to have both the surface roughness $R_a$ equal to or less than 0.21 μm and the surface roughness $R_y$ equal to or less than 1.49 μm.

For example, the configuration material of the shaft 62 can be selected from the materials exemplified above as the configuration material of the housing 26. For example, it is preferable that the shaft 62 is configured to be formed from a ceramic-based material such as alumina ceramic and the like being excellent in abrasion resistance and sliding properties and being advantageous to prevent an occurrence of hemolysis and formation of a thrombus.

The centrifugal pump 10 also includes bearings 70 which are provided at opposite ends of the shaft 62 and respectively and pivotally support the shaft ends 66. Hereinafter, to discriminate the two bearings 70 from each other, the bearing on the lower side, that is, the bearing pivotally supporting the first shaft end 66A is referred to as "the first bearing 70A", and the bearing on the upper side, that is, the bearing pivotally supporting the second shaft end 66B is referred to as "the second bearing 70B". In other words, the first bearing 70A and the second bearing 70B are configured to be pivot bearings.

The shaft 62 is rotatably held between the first bearing 70A and the second bearing 70B in a state where a predetermined bearing preload (i.e., clamping force) is applied in the axial direction by the inside the housing 26. In a case where the bearing preload is excessively small (for example, in a case of being smaller than 30 N), oscillations during rotations of the shaft 62 increase so that hemolysis is more likely to occur.

On the contrary, in a case where the bearing preload with respect to the shaft 62 is significantly higher (for example, in a case of exceeding 60 N), a thrombus is likely to occur, and there is a possibility of damage to a bonded portion between the base 48 of the housing 26 and the cover 50. Therefore, it is preferable that the bearing preload applied to the shaft 62 is set within a proper range (for example, approximately from 30 N to 60 N) when manufacturing the centrifugal pump 10.

The first bearing 70A has a bearing surface 73 which is recessed so as to have a spherical surface shape. The bearing surface 73 of the first bearing 70A comes into contact with the first shaft end 66A. The radius of curvature of the bearing surface 73 of the first bearing 70A is greater than the radius of curvature of the first shaft end 66A. The first bearing 70A is disposed in the recessed first disposition portion 54 which is provided in a central portion of the base 48.

The second bearing 70B has a different bearing surface 73 which is recessed so as to have a spherical surface shape. The bearing surface 73 of the second bearing 70B comes into contact with the second shaft end 66B, and the radius of curvature thereof is greater than the radius of curvature of the second shaft end 66B. The second bearing 70B is disposed in the recessed second disposition portion 60 which is provided in the protruding cylinder portion 58 of the cover 50.

For example, the constituent material of the bearings 70 can be selected from the materials exemplified above as the configuration material of the housing 26. It is preferable that the bearings 70 are formed from polyethylene having an ultra-high molecular weight and being excellent in abrasion resistance and self-lubrication properties.

In the centrifugal pump 10 having the above-described configuration, when blood flows into the housing 26 via the blood inlet port 30, the blood flows into the impeller 28 through the opening 92 provided at the apex portion of the impeller 28, thereby being scattered. Centrifugal force is applied to the scattered blood due to rotations of the impeller 28 so that the blood flows inside the blood induction paths 84 toward the outer circumferential side of the impeller 28. The blood flowing out from the blood induction paths 84 flows between the outer side surface of the impeller 28 and the inner side surface of the housing 26. Thereafter, the blood flows out through the blood outlet port 32.

The centrifugal pump 10 according to the present embodiment basically has a configuration as described above. Hereinafter, an operation and an effect thereof will be described.

As described above, in the centrifugal pump 10 according to the present embodiment, the shaft end 66 has the surface roughness $R_a$ equal to or less than 0.21 μm and/or the surface roughness $R_y$ equal to or less than 1.49 μm. According to the above-described configuration, it is possible to prevent hemolysis from occurring due to sliding between the shaft 62 and the bearing 70, and it is possible to prevent a thrombus from being formed at the shaft ends 66 of the shaft 62.

In order to check the above-described effect of the present invention, the below-described tests (a test related to an occurrence of hemolysis and a test related to formation of a thrombus) have been executed. In each test, the test was performed while having the shafts of Novel Examples 1 to 3 and Conventional Controls 1 and 2 as targets in which the surface roughness $R_a$ and the surface roughness $R_y$ of the shaft end were formed as those in Table 1. Note that, the surface roughness was measured by using a stylus-type surface roughness measuring machine (manufactured by Mitutoyo Corporation).

TABLE 1

|  | Surface Roughness $R_a$ | Surface Roughness $R_y$ | Amount of Hemolysis | Formation of Thrombus |
| --- | --- | --- | --- | --- |
| Example 1 | 0.05 | 0.28 | Small | No |
| Example 2 | 0.18 | 1.31 | Small | No |
| Example 3 | 0.21 | 1.49 | Small | No |
| Control 1 | 0.30 | 2.04 | Great | Present |
| Control 2 | 0.44 | 2.97 | Great | Present |

Figure 4:
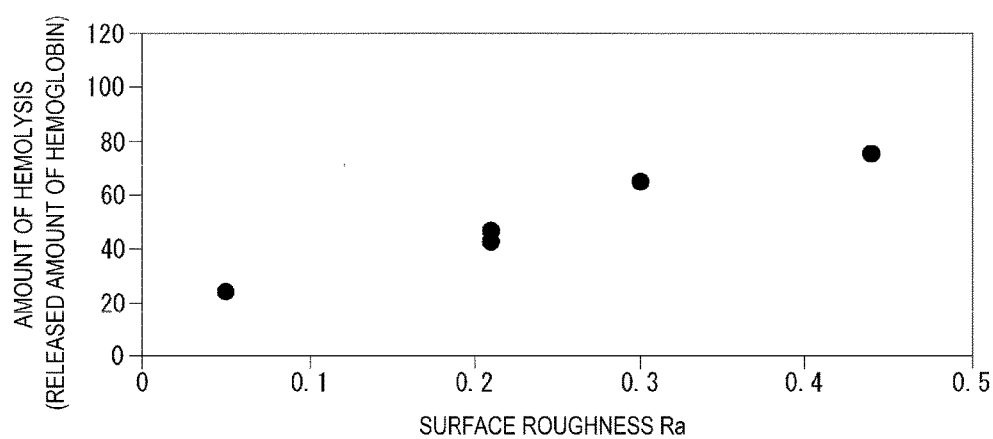
FIG. 4 is a graph illustrating a relationship between surface roughness of a shaft end of a shaft and an amount of hemolysis.

In the test related to an occurrence of hemolysis, while circulating 2.0 L of blood at a flow rate of 8.0 L per minute by using a centrifugal pump in which the test target shafts were applied, the shaft (and the impeller) was continuously rotated for six hours at a rotational frequency of 2,600 rpm. The blood temperature was controlled so as to be at 37° C. FIG. 4 is a graph illustrating the test result related to an occurrence of hemolysis (relationships between the surface roughness $R_a$ and the amount of hemolysis). As seen from FIG. 4, it is ascertained that as the surface roughness $R_a$ of the shaft end becomes smaller, the amount of hemolysis decreases (also refer to the column of "Amount of Hemolysis" in Table 1). In this manner, in Novel Examples 1 to 3, compared to Conventional Controls 1 and 2, it was confirmed that the amount of hemolysis decreased. Note that, since the surface roughness $R_a$ and the surface roughness $R_y$ have a constant correspondence relationship, it is possible to mention that as the surface roughness $R_y$ becomes smaller (i.e., the difference between the highest peak and the lowest valley becomes smaller), the amount of hemolysis decreases.

In the test related to formation of a thrombus, 3 mL (heparin final concentration: 0.5 unit/mL) of blood and the test target shaft were caused to sink in a centrifugation tube, and the centrifugation tube was rotated about the central axial line of the centrifugation tube for six hours at room temperature at a predetermined speed, in a state where the centrifugation tube lay sideways. Thereafter, the presence and the absence, and the degree of a thrombus formed at the shaft end of the shaft were checked.

As a result of the test, in Novel Example 1 ($R_a$=0.05 μm), almost no adhering blood component (platelet or the like) was found and no thrombus was confirmed. In each of Novel Example 2 ($R_a$=0.18 μm) and Novel Example 3 ($R_a$=0.21 μm), it was confirmed that a thin net-like film was slightly formed at the shaft end. Note that, the thin net-like film confirmed in Novel Examples 2 and 3 was not a substance which might be referred to as a fibrin net (fibrin which is a fiber component in blood and is bonded in a mesh pattern), and no thrombus was confirmed. Therefore, it is understood that, in Novel Examples 1 to 3, there is an effect of preventing a thrombus from being formed (also refer to the column of "Formation of Thrombus" in Table 1).

Meanwhile, in Conventional Control 1 ($R_a$=0.30 μm), it was confirmed that a thin fibrin net was formed at the shaft end. In Conventional Control 2 ($R_a$=0.44 μm), it was confirmed that a thick fibrin net was formed at the shaft end. A thrombus is formed due to blood corpuscles or platelets which become entangled with a fibrin net. Therefore, it is understood that, in Conventional Controls 1 and 2, there is no effect of preventing a thrombus from being formed.

According to the test result hereinbefore, it is ascertained that when the surface roughness $R_a$ of the shaft end of the shaft is equal to or less than 0.21 μm, there is an effect of preventing a thrombus from being formed, and as the surface roughness $R_a$ becomes smaller, there is a high effect of preventing a thrombus from being formed. Note that, since the surface roughness $R_a$ and the surface roughness $R_y$ have a constant correspondence relationship, it is possible to mention that as the surface roughness $R_y$ becomes smaller, there is a high effect of preventing a thrombus from being formed.

As it is understood from above, according to the present invention, the surface roughness $R_a$ of the shaft end 66 of the shaft 62 is equal to or less than 0.21 μm (the surface roughness $R_y$ is equal to or less than 1.49 μm). Therefore, it is possible to prevent hemolysis from occurring due to sliding between the shaft 62 and the bearing 70, and it is possible to prevent a thrombus from being formed at the shaft ends 66 of the shaft 62. Particularly, when the surface roughness $R_a$ of the shaft end 66 is equal to or less than 0.21 μm and the surface roughness $R_y$ of the shaft end 66 is equal to or less than 1.49 μm, an effect of preventing an occurrence of hemolysis and formation of a thrombus is more favorably achieved.

In the centrifugal pump 10 which employs the pivot bearings (the bearings 70) as means for supporting rotations of the shaft 62, the rotations of the shaft 62 are considered to be a cause of damage to blood. Therefore, controlling the surface roughness of the shaft end 66 of the shaft 62 leads to controlling of damage to blood. It is considered that formation of a thrombus or hemolysis arising from rotations of the shaft 62 occurs due to ground blood corpuscles, heat generation, shearing stress, and the like caused by friction between the shaft 62 and the bearing 70. It is possible to effectively exclude the above-described factors of formation of a thrombus or hemolysis by setting the surface roughness of the shaft end 66 of the shaft 62 within the above-referenced range.

In addition, in the case of the present embodiment, in each of the first shaft end 66A and the second shaft end 66B, the surface roughness $R_a$ is equal to or less than 0.21 μm (the surface roughness $R_y$ is equal to or less than 1.49 μm). Therefore, it is possible to prevent an occurrence of hemolysis and formation of a thrombus at both ends of the shaft 62. Therefore, it is possible to further enhance a hemolysis prevention effect and a thrombus prevention effect.

In addition, in a case where the shaft 62 is configured to be formed from alumina ceramic, together with a hemolysis prevention effect and a thrombus prevention effect described above and obtained by setting the surface roughness $R_a$ or the surface roughness $R_y$ of the shaft end 66 of the shaft 62, it is possible to more effectively prevent hemolysis from occurring and to prevent a thrombus from being formed.

Note that, in the above-described embodiment, in each of the first shaft end 66A and the second shaft end 66B, the surface roughness $R_a$ is set to equal to or less than 0.21 μm (the surface roughness $R_y$ is set to equal to or less than 1.49 W. However, the surface roughness $R_a$ or the surface roughness $R_y$ of only one between the first shaft end 66A and the second shaft end 66B may be set within the above-referenced range. In this case, in any one between the first shaft end 66A and the second shaft end 66B, it is possible to obtain a hemolysis prevention effect and a thrombus prevention effect described above.

In the above description, a preferred embodiment of the present invention has been exemplified. However, the present invention is not limited to the embodiment, and it is not necessary to mention that various modifications and changes can be made without departing from the scope of the present invention.

What is claimed is:

1. A centrifugal pump comprising:
   a housing;
   an impeller rotatably disposed inside the housing;
   a shaft fixed to the impeller at a center rotational axis of the impeller and having opposing shaft ends, each shaft end having a spherical surface shape; and
   bearings mounted in the housing and pivotally supporting the shaft ends, wherein the bearings each has a recessed bearing surface having a spherical surface shape with a radius of curvature greater than a radius of curvature of the spherical surface shapes of the shaft ends;
   wherein each of the shaft ends with the spherical surface shape has surface roughness $R_a$ equal to or less than 0.21 μm and surface roughness $R_y$ equal to or less than 1.49 μm.

2. The centrifugal pump according to claim 1, wherein the shaft is comprised of alumina ceramic.

3. The centrifugal pump according to claim 1, wherein the bearing preload with respect to the shaft in an axial direction ranges from 30 N to 60 N.

* * * * *